United States Patent [19]
Suzuki et al.

[11] Patent Number: 5,358,619
[45] Date of Patent: Oct. 25, 1994

[54] OXYGEN ELECTRODE

[75] Inventors: Hiroaki Suzuki; Akio Sugama; Naomi Kojima, all of Kawasaki, Japan

[73] Assignee: Fujitsu Limited, Kawasaki, Japan

[21] Appl. No.: 993,486

[22] Filed: Dec. 17, 1992

Related U.S. Application Data

[63] Continuation-in-part of Ser. No. 761,005, Sep. 17, 1991, abandoned.

[30] Foreign Application Priority Data

| | | | |
|---|---|---|---|
| Sep. 17, 1990 | [JP] | Japan | 2-243849 |
| Jun. 6, 1991 | [JP] | Japan | 3-151573 |
| Dec. 20, 1991 | [JP] | Japan | 3-338678 |
| Jul. 22, 1992 | [JP] | Japan | 4-195578 |

[51] Int. Cl.$^5$ .................................. G01N 27/26
[52] U.S. Cl. .................. 204/403; 204/412; 204/415; 204/418; 204/431; 435/817; 435/288
[58] Field of Search ............................ 204/415, 418

[56] References Cited

U.S. PATENT DOCUMENTS

| | | | |
|---|---|---|---|
| 4,437,970 | 3/1984 | Kitajima et al. | 204/412 |
| 4,975,175 | 12/1990 | Karube et al. | 204/403 |

*Primary Examiner*—John Niebling
*Assistant Examiner*—Bruce F. Bell
*Attorney, Agent, or Firm*—Staas & Halsey

[57] ABSTRACT

A small oxygen electrode and a method of bonding a fluorine resin film are disclosed. This small oxygen electrode includes a flat electrode substrate having at least two electrodes (a working electrode and a counter electrode) formed thereon, and a container substrate having dents formed to confront the two electrodes and contain an electrolyte therein. The container substrate which is bonded to the flat electrode substrate, so that the dent confronting the electrode constituting the working electrode has a through hole extending to the side opposite to the flat electrode substrate and a gas-permeable film is formed to cover the through hole. By using this dent structure, the preparation of an oxygen electrode can be conducted while maintaining a wafer form throughout the process, and formation of an electrode pattern can be facilitated. The method of bonding the fluorine resin film includes treating the fluorine resin film with an agent containing metallic sodium, then treating the fluorine resin film with a silane coupling agent. The treated fluorine resin film is fusion bonded by heating, and if necessary, conducting subsequent treatments in vacuo. By adopting this method, the fluorine resin film can be bonded tightly to the substrate and peeling of the fluorine resin film from the substrate can be prevented.

24 Claims, 14 Drawing Sheets

OXYGEN ELECTRODE

CROSS REFERENCE TO RELATED APPLICATION

This application is a continuation-in-part of U.S. application Ser. No. 07/761,005, filed Sep. 17, 1991, now abandoned.

BACKGROUND OF THE INVENTION

1. Field of the Invention

The present invention relates to an oxygen electrode and a process for the preparation thereof. More particularly, the present invention relates to a small oxygen electrode fabricated by utilizing a micro-machining technique and a process for the preparation thereof. Furthermore, the present invention relates to a method of bonding a fluorine resin film onto a substrate. More particularly, the present invention relates to a method of bonding a fluorine resin film tightly to a silicon wafer, a glass substrate or the like in the field of the semiconductor process or micro-machining.

2. Description of the Related Art

Oxygen electrodes are advantageously used for the measurement of the dissolved oxygen concentration. For example, the biochemical oxygen demand (BOD) in water is measured from the viewpoint of maintenance of the water quality. An oxygen electrode can be used as a device for measuring this dissolved oxygen concentration. Furthermore, in the fermentation industry, in order to advance the alcoholic fermentation at a high efficiency, it is necessary to adjust the dissolved oxygen concentration in a fermenter, and a small oxygen electrode can be used as means for measuring this dissolved oxygen concentration. Moreover, a small disposable oxygen sensor is demanded in the medical field. Still further, a small oxygen electrode can be combined with an enzyme to construct an enzyme electrode, and this enzyme electrode can be used for measuring the concentration of a saccharide or an alcohol. For example, glucose reacts with dissolved oxygen in the presence of an enzyme called glucose oxidase and is oxidized to gluconolactone. By utilizing the phenomenon that the amount of dissolved oxygen diffused in an oxygen electrode cell is reduced by this reaction, the glucose concentration can be determined from the amount of dissolved oxygen consumed.

As is seen from the foregoing description, the small oxygen electrode can be used in various fields such as environmental instrumentation, the fermentation industry and clinical medical treatment, especially in a case where the small oxygen electrode is attached to a catheter and is inserted into the body. Since the size is small and the electrode is disposable and cheap, the utility value is very high.

Since the size cannot be reduced in commercially available oxygen electrodes and mass production is impossible, the present inventors developed a new small oxygen electrode fabricated by a lithographic technique and an anisotropic etching technique and filed a patent application for this oxygen electrode (U.S. Pat. No. 4,975,175 corresponding to Japanese Unexamined Patent Publication No. 63-238548, see FIGS. 7 through 9). The oxygen electrode of this type has a structure in which two electrodes, that is, an anode 4 and a cathode 5, are formed on a hole 2 formed on a silicon substrate 1 by anisotropic etching through an insulating film 3. An electrolyte-containing liquid 6 is contained in this hole and finally, the top surface of the hole is covered with a gas-permeable (membrane) film 7. In the drawings, reference numeral 8 represents a responding part and reference numeral 9 represents a pad. This small oxygen electrode is small in size and the dispersion of characteristics is small. Moreover, since mass production is possible, the manufacturing cost is low.

Thus, conventional small oxygen electrodes have been improved almost to a practically applicable level by making improvements to the materials used for the fabrication. However, there are still some unsolved problems for preparing small oxygen electrodes along a manufacturing line and marketing them, as described below.

(1) In many cases, it is difficult to selectively form an electrolyte layer and a gas-permeable layer. Accordingly, the number of operations conducted for each chip is increased and the productivity is reduced. Therefore, the price of the small oxygen electrode rises.

(2) The operation of forming an electrode pattern from above the hole formed by anisotropic etching toward the bottom becomes difficult as the step depth increases, and the precision of formation of the pattern is reduced and special means such as lap baking becomes necessary. Accordingly, the fabrication is very troublesome.

(3) In conventional small oxygen electrodes, since the gas-permeable film is directly formed on the responding part, an electrode infiltrated into a gel or a polymeric solid electrolyte is used. However, it is difficult to regulate precisely the quantity of the electrolyte and, as a result, the dispersion of characteristics is adversely influenced.

(4) A gas-permeable film was formed at the outset by dip coating or spin coating a liquid material. Most of materials used for such gas-permeable films (silicone resins and the like) deteriorate over time because the storage stability per year cannot be guaranteed.

(5) It is sufficient if the gas-permeable film is spread only in the vicinity of the working electrode, but in the above-mentioned oxygen electrode, where only one silicon substrate is used as the substrate, the gas-permeable film should also be formed in an irrelevant portion such as an anode region, and the gas-permeable film is readily damaged.

In the field of semiconductor processing or micro-machining, it is demanded that a fluorine resin film, for example, as a gas-permeable film or an insulating material, should be tightly bonded to a silicon wafer or a glass substrate, as in the case of a small Clark cell (barrier membrane type) fabricated by utilizing the micro-machining technique.

As previously pointed out, a small oxygen electrode can be used in the fields of environmental instrumentation, the fermentation industry and clinical medical treatment, especially in a case where the small oxygen electrode is attached to a catheter and is inserted into the body. Since the size is small and the electrode is disposable and cheap, the utility value is very high.

In the production of a small oxygen electrode, for example, a small oxygen electrode disclosed in U.S. Pat. No. 4,975,175 corresponding to Japanese Unexamined Patent Publication No. 63-238548, formation of a gas-permeable film is accomplished by forming a water-repellant polymer film by dip coating or spin coating, and in the latter case, bonding a fluorine type fluorinated ethylene propylene (FEP) film by heat fusion. The process disclosed in Japanese Unexamined Patent Publication No. 63-238548 is simple, but the process is defective in that it is generally difficult to reconcile the selective formation of a film pattern with an increase of the film strength.

In the conventional semiconductor process, there is known a method of bonding a fluorine resin as an insulating material to a silicon wafer or a glass substrate where fusion bonding is carried out at the fluorine resin-melting temperature (about 280° C.). However, the film formed by this method is readily peeled by incorporation of bubbles at the fusion bonding, change of the temperature or friction, and the resistance to wetting with water is very low.

In the case where a biosensor such as a small sensor is used in the medical field, the sensor should be subjected to high-pressure vapor sterilization in advance. Peeling of the gas-permeable film is frequently caused at this high-pressure vapor sterilization, and this is a very serious practical problem.

SUMMARY OF THE INVENTION

It is a primary object of the present invention to provide an oxygen electrode and a method of bonding a fluorine resin film, by which the foregoing problems can be solved.

In accordance with one aspect of the present invention, this object can be attained by an oxygen electrode comprising a flat electrode substrate having at least two electrodes (a working electrode and a counter electrode) formed thereon, and a container substrate having dents formed to confront the two electrodes and contain an electrolyte therein, bonded to said flat electrode substrate, wherein of said dents, the dent confronting the electrode constituting the working electrode has a through hole extending to the side opposite to the flat electrode substrate and a gas-permeable film is formed to cover said through hole.

In accordance with another aspect of the present invention, there is provided a process for the preparation of an oxygen electrode, which comprises bonding a flat electrode substrate having at least two electrodes (a working electrode and a counter electrode) formed thereon to a container substrate having an electolyte-injecting dent confronting the counter electrode and a through hole formed at the position confronting the working electrode, covering the through hole with a gas-permeable film to form a hole, and injecting an electrolyte into said dent and said hole.

In accordance with still another aspect of the present invention, there is provided a method of bonding a fluorine resin film which comprises treating the surface of the fluorine resin film with an agent containing metallic sodium, further treating the surface with a silane coupling agent, and fusion-bonding the treated fluorine resin film to a substrate by heating.

In accordance with a further aspect of the present invention, there is provided a method of bonding a fluorine resin film, which comprises treating the surface of a substrate with a silane coupling agent, and fusion-bonding the fluorine resin film to the treated surface by heating.

BRIEF DESCRIPTION OF THE DRAWINGS

The object as well as advantages of the present invention will become clear by the following description of preferred embodiments of the present invention with reference to the accompanying drawings, in which:

FIGS. 11A, 11B, 11C are sectional views showing the section of the oxygen electrode of FIG. 10, wherein FIG. 11A is a sectional view taken along a line A—A of FIG. 10, FIG. 11B is a sectional view taken along a line B—B and FIG. 11C is a sectional view taken along a line C—C;

FIGS. 12A, 12B, 12C and 12D are explanatory views useful for explaining the fabrication process of the oxygen electrode shown in FIG. 11, wherein FIG. 12A shows a silicon wafer having an $SiO_2$ insulating film formed thereon after etching, FIG. 12B shows the state where an electrode sensitive portion is defined, FIG. 12C shows the state where a gas-permeable film is formed, and FIG. 12D shows the state where an electrolyte is filled into the sensitive portion.

DETAILED DESCRIPTION OF THE PREFERRED EMBODIMENTS

Figure 1:
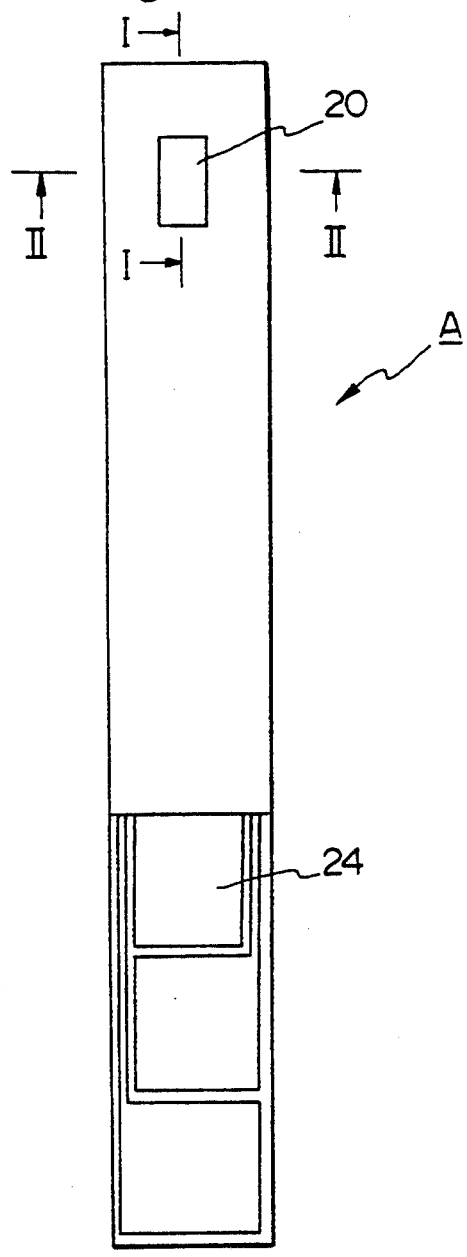
FIG. 1 is a plane view showing a small oxygen electrode according to one embodiment of the present invention.

As pointed out hereinbefore, the size of the oxygen electrode is very small, and the basic technique of micro-machining is adopted for the preparation of this small oxygen electrode.

The process of the present invention utilizing this basic technique is characterized by the following features.

(1) Two substrates are used, and respective substrates are independently processed and bonded together to complete an oxygen electrode.

(2) The step of forming an electrolyte is omitted. Namely, the electrolyte is not charged by a manufacturer of the small oxygen electrode, but is injected by a user just before using.

(3) Electrode patterns of a working electrode, a reference electrode, a counter electrode and the like are formed with no deep steps, but they are formed on a substantially plane substrate.

(4) A through hole is formed only at a part of the working electrode and a gas-permeable film is coated only at this part.

(5) The gas-permeable film is bonded by heat fusion bonding or the like.

This oxygen electrode of the present invention can be fabricated by bonding the electrode substrate and the container substrate.

At least two electrodes, that is, a working electrode (first electrode) and a counter electrode (second electrode), are formed on the flat electrode substrate.

In the case of a two-electrode structure, there are formed a cathode and an anode, and the cathode acts as the working electrode and the anode acts as the counter electrode.

The cathode and anode can be varied according to whether the electrode to be manufactured is of the polaro-type or the galvanize type. For example, in the production of an oxygen electrode of the polaro-type, both the electrodes are constructed by gold electrodes or platinum electrodes, or an anode is constructed as the reference electrode, and a voltage is applied between both the electrodes at the measurement. In case of an oxygen electrode of the polaro-type, a neutral aqueous solution such as a 0.1M aqueous solution of potassium chloride that hardly corrodes the silicon container portion is preferably used as the electrode. Furthermore, if an electrode of a metal more chemically reactive than gold or platinum, such as lead or silver, is used as the anode side electrode, an electrode of gold, platinum or the like is used as the cathode side electrode. In this case, an alkaline aqueous solution such as a 1M aqueous solution of potassium hydroxide is used as the electrolyte, and a galvanic oxygen electrode can be prepared.

In the case of a three-electrode structure, a reference electrode is further formed, and the working electrode and counter electrode are constructed by gold or platinum electrodes and a silver/silver chloride reference electrode or the like is preferably used as the reference electrode. These electrodes can be advantageously formed by such a film-forming method as vacuum evaporation deposition or sputtering.

Various solutions such as an aqueous solution of potassium chloride, an aqueous solution of potassium hydroxide and an aqueous solution of sodium sulfate can be used as the electrolyte.

It is indispensable that the gas-permeable film should be hydrophobic and should not allow permeation of an aqueous solution, and it also is important that the gas-permeable film should be bonded tightly with a good adhesion to a silicon substrate or a silicon oxide substrate by heat fusion bonding or the like. FEP and silicone varnish films can be preferably used as the gas-permeable film.

Preferred embodiments of the oxygen electrode of the present invention will now be described.

A reference electrode is formed on the flat electrode substrate in addition to a working electrode and a counter electrode, and a dent for injection of an electrolyte is formed on the container substrate.

The electrodes formed on the flat electrode substrate are preferably separated from one another to such an extent that they are not influenced by products formed on the surfaces of the respective electrodes.

As preferred examples of the material constituting the flat electrode substrate, there can be mentioned a Pyrex glass substrate, a lead glass substrate, a silicon substrate having a film of a Pyrex glass-containing borosilicate glass formed on the surface thereof, a silicon substrate having a lead glass film formed on the surface thereof, a glass substrate having a film of a Pyrex glass-containing borosilicate glass formed on the surface thereof, a glass substrate having a lead glass film formed on the surface thereof, and a silicon substrate having a thermally oxidized film on the surface thereof.

A pad is preferably formed at one end of each electrode formed on the electrode substrate, and the size of the pad is such that a socket terminal or the like of IC can be used in the state directly gripped in the pad.

A semiconductor substrate, especially a silicon substrate, is advantageously used as the material of the container substrate. A (100) plane silicon substrate is especially preferably used as the silicon substrate.

When a silicon substrate is used, an insulating film can be constructed by a silicon oxide film or the like. For example, when the substrate is composed of silicon, a silicon oxide film can be easily formed by thermal oxidation of the substrate. A silicon nitride film has very good properties as the insulating film, but since anode junction (bonding) is impossible, the silicon nitride film cannot be used for the junction surface.

Respective dents for containing the electrolyte, formed in the container substrate, can be connected to each other through a long groove.

Furthermore, in the oxygen electrode of the present invention, it is preferred that the electrodes be formed in a shallow groove flatly etched in accordance with the electrode pattern.

On the front surface of the container substrate, that is, on the surface opposite to the surface to be bonded to the electrode substrate, a dent is formed in the peripheral edge portion of the through hole formed in the container substrate, and this dent is preferably covered with a gas-permeable film. If this structure is adopted, the distance between the gas-permeable film and the working electrode becomes much shorter and the sensitivity of the oxygen electrode per se can be improved.

A tetrafluoroethylene/hexafluoroethylene copolymer (FEP) film is preferably used as the gas-permeable film, and the thickness of this film is preferably smaller than 20 $\mu$m.

A gold electrode, a platinum electrode, a carbon electrode and the like are preferably used as the working electrode (cathode), and similarly, a gold electrode, a platinum electrode, carbon electrode and the like are preferably used as the counter electrode (anode). Furthermore, a silver/silver chloride electrode is preferably used as the reference electrode.

An aqueous solution of potassium chloride, an aqueous solution of potassium hydroxide and the like are preferably used as the electrolyte.

The small oxygen electrode of the present invention is used in the state where a certain voltage negative to the counter electrode (anode) or the reference electrode is applied to the working electrode (cathode). In the state where the responding part of this small oxygen electrode is immersed in a buffer solution, dissolved oxygen permeates through the gas-permeable film and arrives at the working electrode (cathode) where reduction is effected. If the value of a current generated at this point is measured, the dissolved oxygen can be known with the current value as a criterion.

The method of bonding a fluorine resin film according to the present invention will now be described in detail. As a result of research made with a view to solving the above-mentioned problems, the present inventors found that the problems can be solved by two means described below. The present invention has now been completed based on this finding.

According to the first means, the surface of a fluorine resin or the surface of a silicon wafer is chemically modified to form a chemical bond between them, whereby the bonding force is increased.

A fluorine resin is characterized in that it has no reactivity, but if only fluorine present in the surface portion is isolated and the surface is treated with a silane coupling agent, a chemical bond is formed between the fluorine resin and the silicon wafer, and tight bonding becomes possible.

Namely, the first means of the present invention is characterized in that the surface of a fluorine resin film is treated with an agent containing metallic sodium, the surface is then treated with a silane coupling agent and the treated fluorine resin film is fusion-bonded to a substrate by heating, or the surface of a substrate is treated with a silane coupling agent and a fluorine resin film is fusion-bonded to the treated substrate by heating. In the latter method, a fluorine resin film treated with an agent containing metallic sodium can be used as the fluorine resin film, or a fluorine resin film treated with an agent containing metallic sodium and then treated with a silane coupling agent can be used as the fluorine resin film.

The second means is to cope especially with the latter problem described hereinbefore. It was found that at the fusion bonding of a fluorine resin film, air bubbles are left between the fluorine resin film and the substrate to reduce the bonding area between the film and substrate. At the high-pressure vapor sterilization, the bubbles are inflated to cause peeling of the film. It also was found that this problem of peeling can be solved by removing the air bubbles in vacuo or by carrying out the operation in vacuo throughout the fusion bonding.

The second means of the present invention is characterized in that the surface of a fluorine resin film is treated with an agent containing metallic sodium and is then treated with a silane coupling agent. The treated fluorine resin film is fusion-bonded to a substrate by heating. The fusion-bonded substrate is allowed to stand still in vacuo, and the fusion-bonded substrate is placed under atmospheric pressure and the substrate is fusion-bonded again. In addition, or alternatively, the surface of a fluorine resin film is treated with an agent containing metallic sodium and is then treated with a silane coupling agent, the treated fluorine resin film is fusion-bonded to a substrate in vacuo by heating, the fusion-bonded substrate is allowed to stand in vacuo and the fusion bonding is then carried out in vacuo again.

In the present invention, the term "substrate" means a silicon wafer, a glass substrate and the like, and the term "silane coupling agent" means silicone compounds such as γ-APTES (γ-aminopropyltriethoxysilane) and hexamethyldisilazane.

The present invention will now be described in detail with reference to the following examples that by no means limit the scope of the invention.

EXAMPLES

To begin with, one preferred example of the process for the preparation of a small oxygen electrode according to the present invention will be described with reference to FIGS. 1 through 4 of the accompanying drawings.

FIG. 1 is a plane view showing a small oxygen electrode A of the present invention.

Referring to FIGS. 1–4, the illustrated oxygen electrode has a rectangular shape, and a responding part (working electrode portion) is covered with a gas-permeable film 20 and for connection to accessory devices, parts of a working electrode 21, a counter electrode 22 and a reference electrode 23 are exposed to form a pad 24. The shown electrode can have a two-electrode structure comprising only the working electrode 21 and counter electrode 22. Alternatively, a three-electrode structure further comprising the reference electrode 23 composed of a silver/silver chloride electrode can be adopted.

Figure 2A:
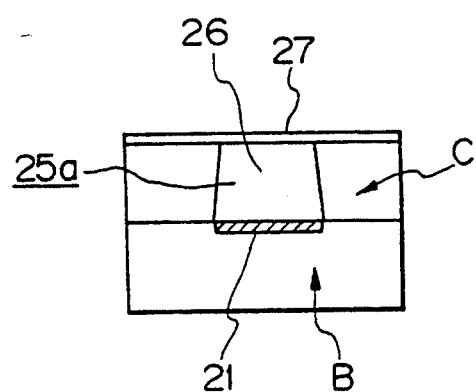
FIG. 2(A) is a cross-sectional view showing the section cut along line II—II in FIG. 1.
Figure 2B:
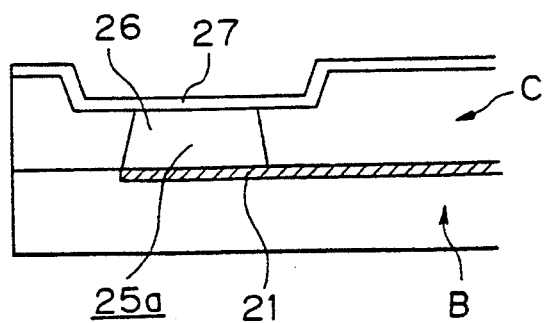
FIG. 2(B) is a cross-sectional view showing the section cut along line I—I in FIG. 1.
Figure 3:
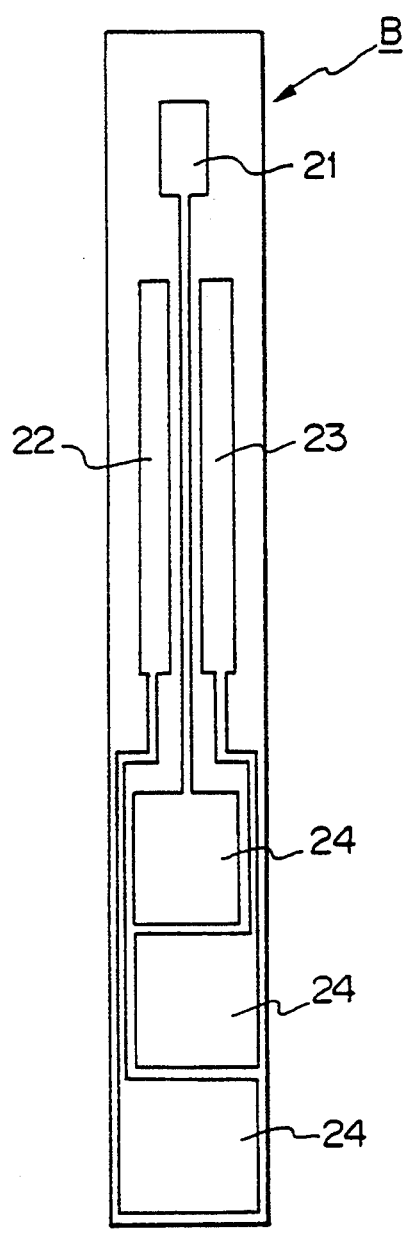
FIG. 3 is a plane view showing an electrode substrate constituting the oxygen electrode shown in FIG. 1.
Figure 4:
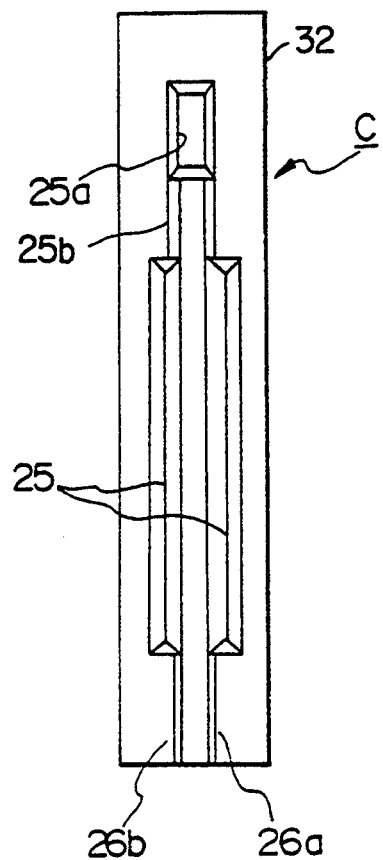
FIG. 4 is a plane view showing a container substrate constituting the oxygen electrode shown in FIG. 1.

The structure of the small oxygen electrode shown in FIG. 1 will be readily understood from FIGS. 3 and 4. More specifically, the working electrode 21, counter electrode 22 and reference electrode 23 are formed on an electrode substrate B composed of a glass. Dents 25 for storing electrolytes 26a and 26b are formed on a container substrate C at parts confronting the working electrode 21, counter electrode 22 and reference electrode 23, by anisotropic etching. The dent 25a at the part confronting the working electrode 21 is formed to pierce through a silicon substrate 32 to the opposite side for formation of a gas-permeable film 27 (FIG. 2(A)). Namely, the gas-permeable film 27 is formed on the top face of the dent 25a. Respective holes are connected to one another through fine grooves 25b. An electrolyte, for example, 0.1M KCl, is filled in the dents of the container substrate C after fabrication, and injection grooves 26a and 26b are formed in the vicinity of the pad 24 for injecting this electrolyte into fine holes.

The oxygen electrode A of the present invention is fabricated by bonding the electrode substrate B and the container substrate C together so that the electrodes formed on the electrode substrate B confront the dents formed in the container substrate C. FIG. 2(A) shows the section II—II of the so-fabricated oxygen electrode A.

The small oxygen electrode shown in FIG. 1 can be advantageously prepared according to the preparation process steps shown in sequence in FIG. 5. In the description given below, an embodiment where one oxygen electrode is formed for one wafer is explained to facilitate the understanding, but it should be noted that practically, many small oxygen electrodes are simultaneously formed. In FIG. 5, only the vicinity of the working electrode is illustrated, but it should be noted that other portions are similarly formed.

(I) Preparation of Electrode Substrate (1) A negative photoresist film having the same pattern as that of a working electrode (cathode), a counter electrode (anode) and a reference electrode, to be formed afterward, is formed on a so-called 2-inch Pyrex glass (Iwaki Glass 7740) substrate 30 in such a manner that the glass is exposed in electrode-forming areas.

(2) The same negative photoresist is coated on the entire back surface and baking is carried out at 150° C. for 30 minutes.

(3) A wafer is immersed for 1 hour in a mixed solution comprising 50% fluoric acid, concentrated nitric acid and 40% ammonium fluoride at a ratio of 1/1/8 to etch the exposed glass. The etching depth is 3 $\mu$m.

Figure 5A:
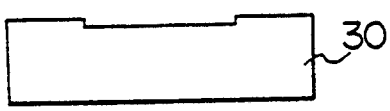
FIGS. 5(a), 5(b), 5(c), 5(d), 5(e), 5(f), and 5(g) are diagrams showing steps of the preparation of the oxygen electrode shown in FIG. 1 in regular sequence.

(4) The negative photoresist film formed through the steps (1) and (2) is peeled in a mixed solution comprising sulfuric acid and hydrogen peroxide at a ratio of 2/1 (see FIG. 5(a)).

(5) The substrate is sufficiently washed with a mixed solution of hydrogen peroxide and ammonia and then with pure water, and is then dried.

(6) A gold film is formed on the substrate by vacuum evaporation deposition. Since the adhesion between gold and glass is very poor, a thin chromium layer is interposed to improve the adhesion. The thickness of the chromium layer is 40 nm and the thickness of the gold layer is 400 nm.

(7) A positive photoresist film (OFPR-5000 supplied by Toyo Oka) is formed on the gold-deposited surface of the substrate.

(8) By using the same pattern as used at the step (1), a working electrode (cathode) pattern and a counter electrode (anode) pattern are formed.

(9) The resist pattern-formed substrate is immersed in a gold-etching solution formed by dissolving 4 g of KI and 1 g of $I_2$ in 40 ml of water to remove the exposed gold portion by etching. Then, the substrate is washed with pure water and the resist is removed by acetone.

(10) The substrate is immersed in a chromium-etching solution formed by dissolving 0.5 g of NaOH and 1 g of $K_3Fe(CN)_6$ in 4 ml of water to remove the exposed chromium portion.

(11) The substrate is sufficiently washed with pure water and is then dried.

In case of a two-electrode system comprising gold electrodes alone, the preparation terminates at the above step. However, in case of a three-electrode system, a reference electrode is further formed through the following steps.

(12) Silver is vacuum-deposited in a thickness of 400 nm on the substrate obtained at the step (11). In view of the adhesion, it is preferred that in the state of the step (11), the pattern of the gold electrode also be formed on the portion of the reference electrode. In the case where the gold pattern is located below, the Cr layer interposed at the step (6) becomes unnecessary.

(13) A positive photoresist is coated on the surface of the substrate, and after baking, light exposure and development, a photoresist pattern is formed only at a part where the reference electrode is to be formed.

(14) The entire substrate is immersed in a mixed solution comprising 29% ammonia, 31% hydrogen peroxide and pure water at a ratio of 1/1/20 to effect etching of silver.

(15) The substrate is sufficiently washed with pure water, and the entire substrate is immersed for 10 minutes in a 0.1M solution of $FeCl_3$ to form a thin layer of silver chloride on the surface of silver.

(16) The entire substrate is sufficiently washed with pure water.

Figure 5C:
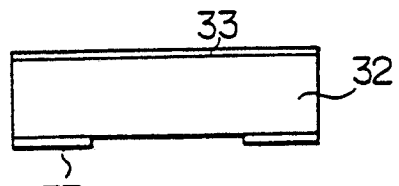
Figure 5B:
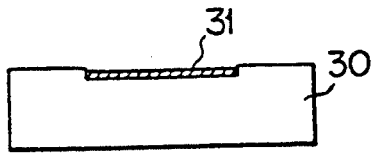

The electrode substrate is completed through the steps (1) to (16) (see FIG. 5(b)). Incidentally, in FIG. 5(b), reference numeral 31 represents the working electrode (cathode).

(II) Preparation of Container Substrate (1) A 2-inch (100) plane silicon wafer 32 having a thickness of 350 $\mu$m is prepared, and the wafer is washed with a mixed solution of hydrogen peroxide and ammonia and with concentrated nitric acid.

(2) The silicon wafer 32 is subjected to wet thermal oxidation at 1050° C. for 200 minutes to form an $SiO_2$ film 33 having a thickness of 1.0 $\mu$m on the entire surface.

(3) A negative photoresist (OMR-83 supplied by Tokyo Oka) having a viscosity of 60 cP is coated on the smooth surface of the silicon substrate, and light exposure, development and rinsing are carried out to form a resist pattern for etching on the wafer.

(4) The wafer is immersed in a mixed solution comprising 50% fluoric acid and 40% ammonium fluoride at a ratio of 1/6 to etch the exposed $SiO_2$ portion [see FIG. 5(c)].

(5) The negative photoresist film formed through the steps (1) and (2) is peeled in a mixed solution comprising sulfuric acid and hydrogen peroxide at a ratio of 2/1.

(6) The substrate is immersed in 35% KOH maintained at 80° C. to effect anisotropic etching of silicon and form dents corresponding to the electrode patterns prepared in the process (I). When the dent patterns are complicated, the steps (1) through (6) are repeated a number of times. Finally, a container substrate having electrolyte-storing cavities in the portions confronting the counter electrode and reference electrode and a through hole 34 in the portion confronting the working electrode is obtained.

(7) If $SiO_2$ used as the mask is left on the surface on the silicon, since a higher temperature is necessary for the anode bonding (III) described below, $SiO_2$ is completely removed in the etching solution used at the step (4).

Figure 5D:
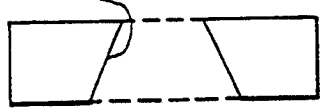

The electrolyte-storing container substrate, is completed through the steps (1) to (7) (see FIG. 5(d)).

(III) Bonding of Electrode Substrate and Container Substrate (1) The electrode substrate completed by the process (I) is subjected to ultrasonic washing in pure water, and the electrolyte-storing container substrate completed by the process (II) is sufficiently washed with an aqueous solution of hydrogen peroxide/ammonia and with pure water.

(2) Registration of the pattern of the electrode-forming surface, obtained in the process (I), with the pattern of the surface having dents formed thereon by etching in the process (II) is carried out in a clean atmosphere.

Figure 5E:
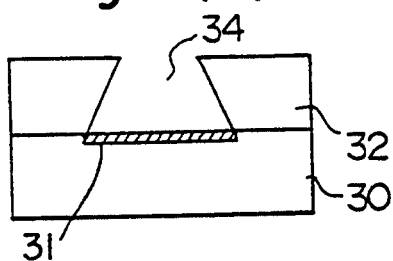

(3) A voltage of 1200 V is applied between the substrates at a temperature of 250° C. to effect anodic bonding between the electrode substrate and the container substrate, so that the electrode substrate is located on the negative side (see FIG. 5(e)).

(IV) Formation of Gas-Permeable Film (1) A gas-permeable film (for example, FEP film having a thickness of 12 μm (supplied by Toray)) is cut in an appropriate size on the surface, opposite to the bonded surface, of the container substrate prepared by the process (II) in the portion where the through hole is formed.

Figure 5F:
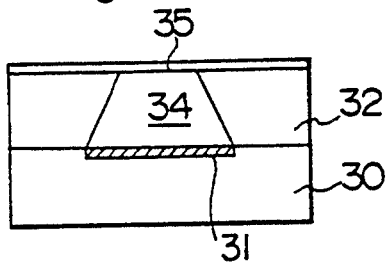

(2) The substrate which has passed through the step (1) is heated at a temperature where FEP melts, whereby the FEP film 35 is bonded to the substrate (see FIG. 5(f)).

(V) Cut-Out of Substrate (1) The substrate having many oxygen electrodes formed thereon is cut out into chips by a dicing saw.

(VI) Injection of Electrolyte

When the size of holes formed within the small oxygen electrode is small, injection of the electrolyte 36 can be accomplished by immersing the small oxygen electrode in 0.1M KCl and placing the entire electrolyte under a reduced pressure. If injection is difficult by this method, the following operation is carried out to facilitate the injection.

(1) The electrolyte is charged in a beaker, and the portion of the electrolyte-injecting groove of the small oxygen electrode is placed in the electrolyte and the portion of the gas-permeable film is placed in the gas phase. In this state, the electrolyte and the beaker are charged in the sealed container and deaeration is carried out by a vacuum pump.

(2) After the container has been allowed to stand still for a while, air is abruptly introduced into the container substrate. By this operation, the electrolyte 36 is introduced at a time to the point where the gas-permeable film is present.

(3) In the case wherein bubbles are left in the portion of the gas-permeable film, the above operations (1) and (2) are repeated.

For injection of the electrolyte, there can also be adopted a method in which sodium alginate containing the electrolyte is charged in the dents and through hole of the oxygen electrode, the entire oxygen electrode is immersed in an aqueous solution of calcium chloride to fill the aqueous solution into the dents and through hole and to gel sodium alginate to calcium alginate, and the oxygen electrode is immersed in the above aqueous solution of the electrolyte, whereby the electrolyte is sufficiently filled into the oxygen electrode. If the dents are too long to gel the sodium alginate in a short time, the procedure can be reversed. Namely, the dents and throughhole are first charged with calcium chrolide solution, the entire electrode is baked to evaporate water in the solution, and then sodium alginate solution containing the electrolyte is charged into the cavity to obtain the gel. Alternatively, the oxygen electrode is immersed in a fused agarose gel containing the electrolyte, and the gel can be introduced into the dents and through hole in the interior of the oxygen electrode.

Figure 5G:
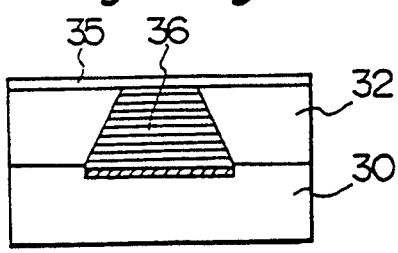

After these operations, a small oxygen electrode capable of practically working can be provided (see FIG. 5(g)).

(VII) Connection to External Meters

When the so-fabricated small oxygen electrode is used, it is necessary to connect the small oxygen electrode to an exterior amplifier or detector. If a large pad portion is formed as shown in FIG. 1, for example, a fitting portion of an IC socket is taken out, a lead line is attached thereto and the connection is effected through the lead line. In the case where it is apprehended that also the pad portion may be immersed in the solution, a lead line (for example, an aluminum line having a diameter of about 50μ) is bonded to the pad portion, and the pad portion and the lead line portion are insulated with a resin. In the case where a problem arises as regards the bonding strength, there can be adopted a method in which even the pad portion is covered with the container substrate (silicon), a through hole is formed in the pad portion as well as in the responding portion, the top end of the lead line is inserted into the pad portion, and the inserted lead line is fixed with an indium or silver paste and further fixed with an insulating resin.

(VIII) Example of Use of Small Oxygen Electrode

Figure 6:
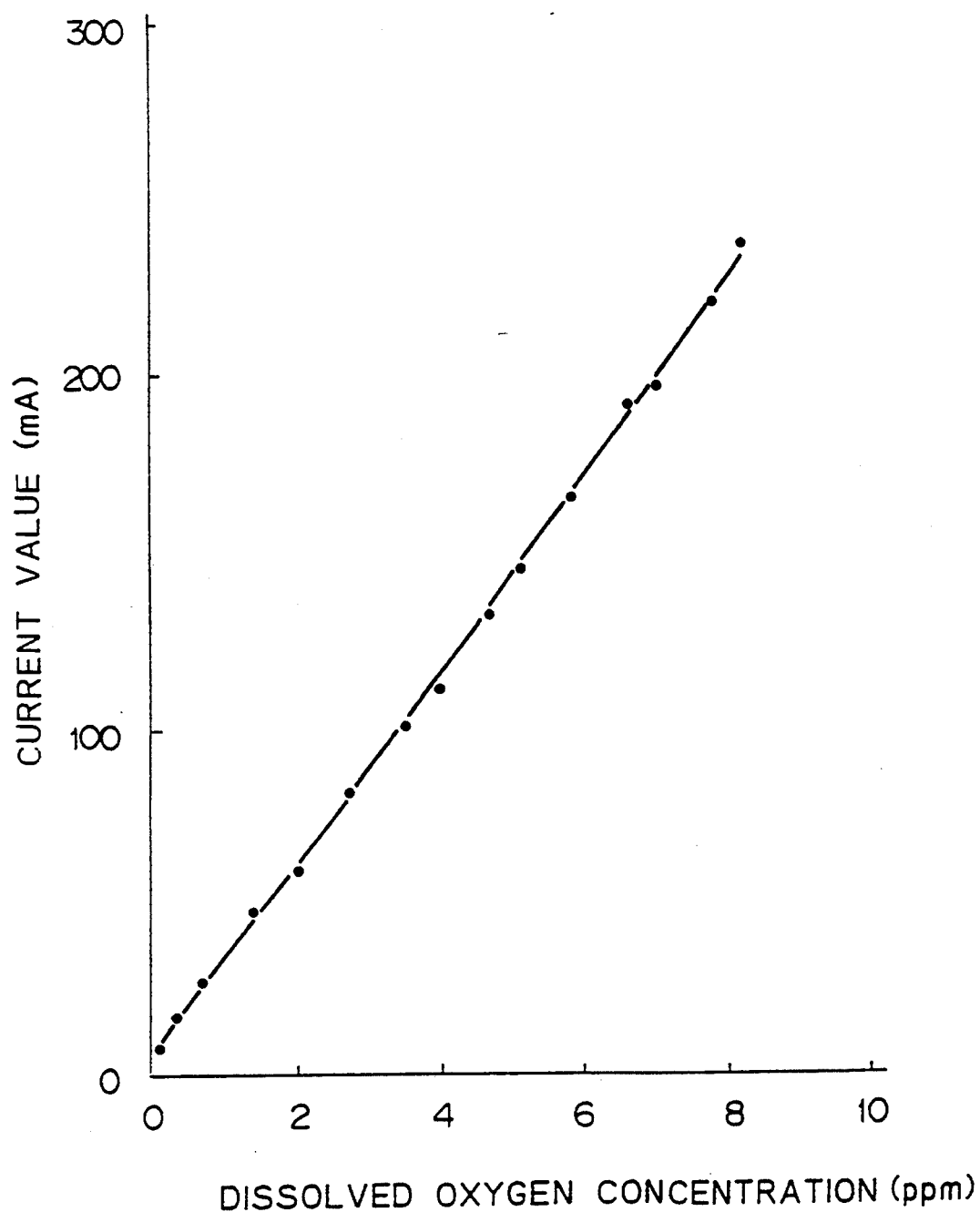
FIG. 6 is a graph showing a calibration curve of the small oxygen electrode of the present invention.
Figure 7:
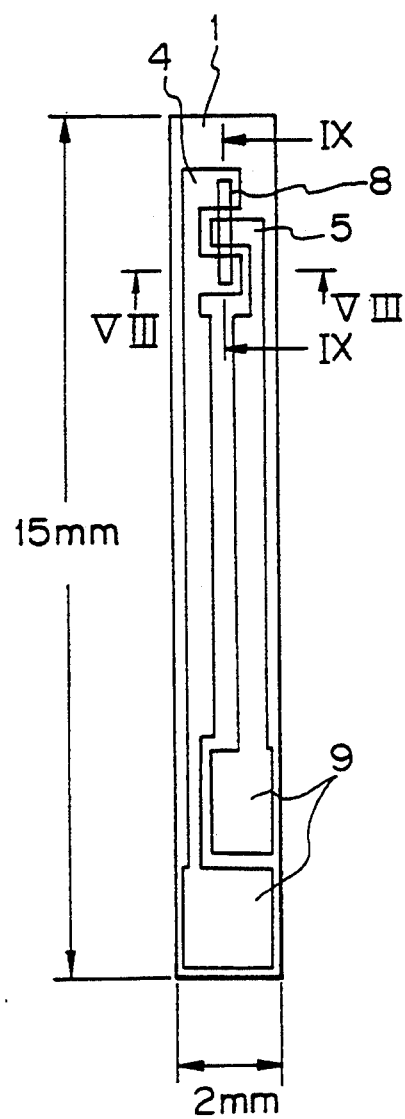
FIG. 7 is a plane view showing a conventional oxygen electrode.
Figure 8:
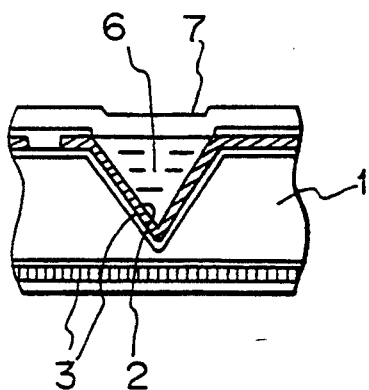
FIG. 8 is a cross-sectional view showing the section taken along line VIII—VIII in the oxygen electrode shown in FIG. 7
Figure 9:
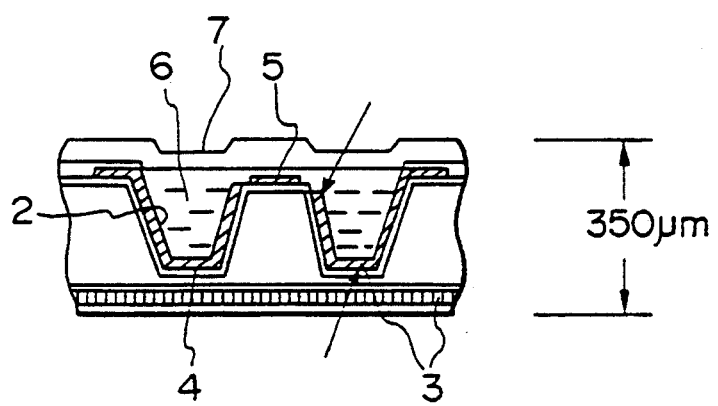
FIG. 9 is a cross-sectional view showing the section taken along line IX—IX in the oxygen electrode shown in FIG. 7.

The characteristics of the above-mentioned small oxygen electrode are examined at 25° C. in a 10 mM phosphate buffer solution having a pH value of 7.0. The applied voltage is $-0.8$ V (vs. Ag/AgCl). As compared with the case of direct injection of a 0.1M KCl electrolyte into the electrode, use of the electrolyte in the state filled in a calcium alginate gel is advantageous, because a stable output is obtained with reduced noise. The 90% responding time is about 2 minutes, and in the state where the dissolved oxygen concentration is 0%, the residual current value is about 7%. The obtained calibration curve is shown in FIG. 6. The dissolved oxygen concentration is lower than 8.2 ppm (the saturation concentration of dissolved oxygen) and a good linearity is observed.

Since the process of the present invention has the above-mentioned structure, the step of forming an electrolyte layer can be omitted. Accordingly, an oxygen electrode can be prepared while maintaining a wafer form throughout the process without any particular trouble, and therefore, an effect of reducing the manufacturing cost can be attained. Moreover, since electrodes are formed on a flat substrate having no deep hole, an electrode pattern can be easily formed. Furthermore, since the electrode can be stored in the dry state free of an electrolyte layer, deterioration of a gas-permeable film is hardly caused. Accordingly, long-prior storage is possible and an area for which the gas-permeable film is necessary is considerably restricted, and therefore, the gas-permeable film is hardly damaged. Still further, since a large quantity of the electrolyte can be stored, the life of the electrode can be prolonged.

The method of bonding a fluorine resin film according to the present invention will be described with reference to the following examples.

EXAMPLE A

An FEP (fluoroethylene-propylene supplied by Toray) film having a thickness of 12 μm was used as the fluorine resin film. The FEP film was washed with ethanol and dried (first step). The washed sample was immersed for 30 seconds in an agent containing Na (Chemgrip supplied by Norton) to effect reaction, and the sample was washed with acetone three times (second step). Then, the sample was immersed for 30 minutes in a 10% aqueous solution of γ-APTES (silane coupling agent composed of γ-aminopropyltriethoxysilane supplied by Aldrich) at 50° C. to effect reaction (third step).

Samples obtained at the respective steps were prepared.

A silicon wafer was used as the substrate, and the untreated silicon wafer (a) and the silicon wafer (b) treated with the silane coupling agent ($\gamma$-APTES) were prepared.

The samples obtained at the respective steps were independently placed on the two wafers (a) and (b), and fusion bonding was carried out on a hot plate maintained at 280° C. Then, in an autoclave, high-pressure sterilization was carried out in water at 120° C. under 2 atmospheres for 15 minutes, and the fusion bonding state was examined.

The bonding ratio after the sterilization is shown in Table 1. With respect to each sample, 10 test pieces were tested. According to the conventional method ((1)-(a)), the film was readily peeled in water. None of the surface-treated samples, other than the sample (2)-(a), were peeled in water, and strong bonding was attained in these samples. Especially, the sample (2)-(b) had a strong bonding force and showed a high resistance in an adhesive cellophane tape peeling test.

TABLE 1

Surface Treatment Conditions and Bonding Ratio (%)

| Fluorine Resin (Si Wafer) | Sample (1) at First Step (untreated) | Sample (2) at Second Step (Na agent) | Sample (3) at Third Step (Na Agent & $\gamma$-APTES) |
|---|---|---|---|
| (a) Untreated | 0 | 0 | 100 ⊚ |
| (b) $\gamma$-APTES | 100 ⊚ | 100 ⊚ | 100 ⊚ |

Note
⊚: very strong

EXAMPLE B

A substrate having a sensor proper, such as a small oxygen electrode, formed thereon was sufficiently subjected to ultrasonic washing in pure water. Then, an FEP (supplied by Toray) film having a thickness of 12 $\mu$m was immersed in a metallic sodium-containing treating agent (for example, Chemgrip) to remove fluorine atoms present on the film surface. Then, the FEP film was further treated with a silane coupling agent ($\gamma$-APTES).

The surface-treated film was placed on the substrate heated at 270° C. to effect fusion bonding. In order to remove bubbles left between the film and the substrate, the substrate to which the film had been fusion-bonded was placed in a vacuum for 5 minutes and immediately, the pressure was returned to atmospheric pressure, and the film-bonded substrate was heated at 270° C. again. This heating operation was repeated as needed. Thus, the adhesion of the film was improved.

In the case where the film is fusion-bonded to a flat substrate, a sufficient strength can be obtained using only the treatment with an agent containing metallic sodium and a silane coupling agent. However, in the case where the film is bonded to a substrate having convexities and concavities on the surface, such as a small practical oxygen electrode, bubbles are often left between the film and the substrate. It is conceivable that such bubbles may be inflated during the high-pressure vapor sterilization treatment to cause peeling of the film, because the contact area between the film and the substrate is reduced and the adhesion is degraded. In this case, a vacuum treatment during the fusion bonding of the film is effective.

The effects attained by the method of Example B are shown in Table 2.

The film treated with metallic sodium and $\gamma$-APTES as described in Example B was fusion-bonded to an untreated silicon wafer, and the vacuum treatment was carried out to complete a small oxygen electrode. Separately, the film treated with an agent containing metallic sodium and $\gamma$-APTES was fusion-bonded to an untreated silicon wafer, but the vacuum treatment was not carried out. The obtained small oxygen electrode was used as a comparative electrode. The two electrodes were subjected to the high-pressure vapor sterilization and then, the states of the films were examined and compared. The obtained results are shown in Table 2.

TABLE 2

Effect by Vacuum Treatment at Fusion Bonding

| | Film Peel Ratio (%) |
|---|---|
| Untreated Sample | 75 |
| Vacuum-Treated Sample | 0 |

From the results shown in Table 2, it is confirmed that a high effect can be attained by the vacuum treatment.

As is apparent from the foregoing description, according to the present invention, by using above-mentioned dent structure, the substrate and the film can be tightly bonded to each other, and peeling of the fluorine resin film from the substrate can be prevented. Especially, in the case where a practical oxygen electrode is once prepared and is then subjected to a severe treatment such as the high-pressure vapor sterilization, according to the method of the present invention including the vacuum treatment, the adhesion of the gas-permeable film is highly improved, and peeling of the film is not caused. Thus, excellent effects can be attained according to the present invention.

Next, a preferred embodiment of the oxygen electrode according to the present invention and its production method will be explained with reference to the accompanying drawings.

Figure 10:
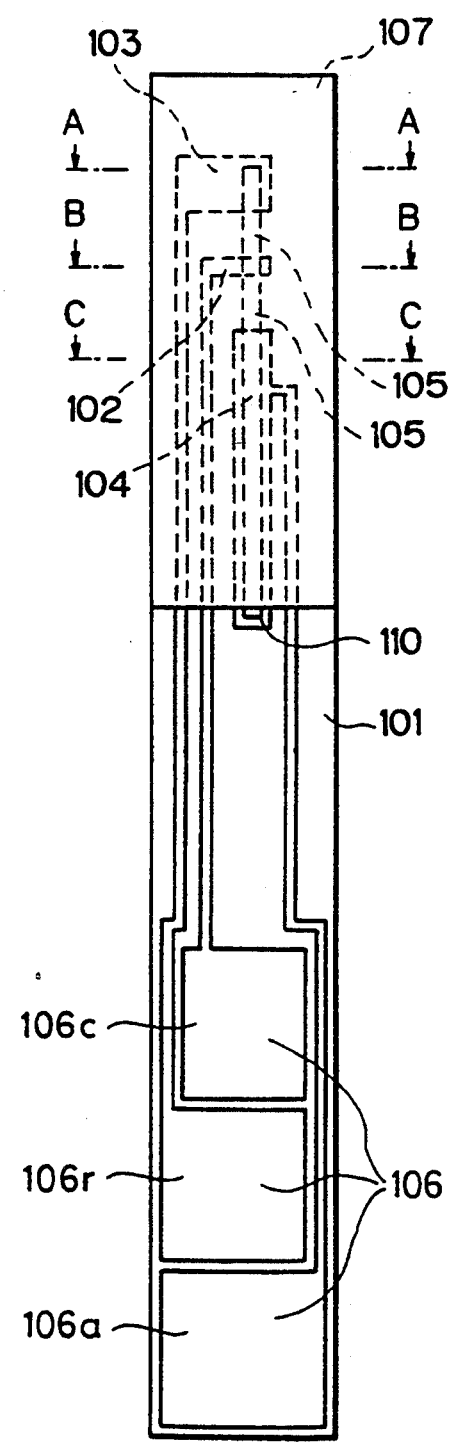
FIG. 10 is a plan view showing an example of the oxygen electrode according to the present invention.
Figure 11A:
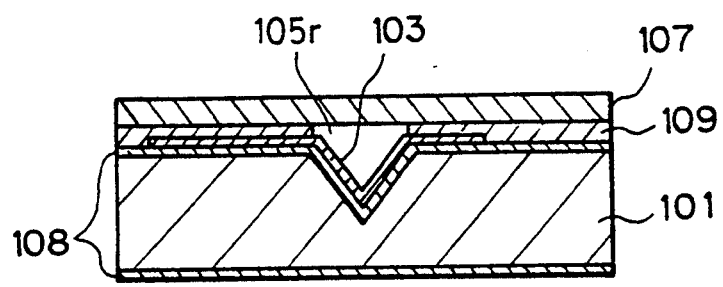
Figure 11B:
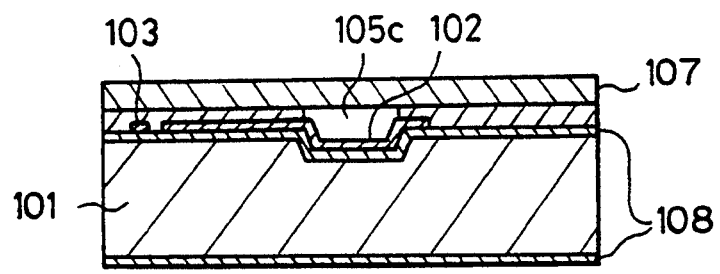
Figure 11C:
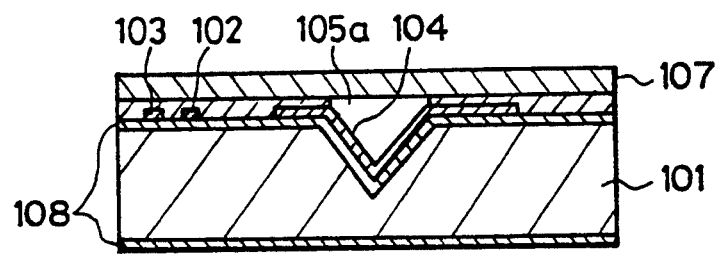

FIG. 10 is a plan view showing a preferred embodiment of the oxygen electrode of the present invention, and FIG. 11 is a sectional view of a sensitive portion of the oxygen electrode. FIG. 11A is a sectional view taken along a line A—A of FIG. 10, FIG. 11B is a sectional view taken along a line B—B of FIG. 10 and FIG. 11C is a sectional view taken along a line C—C of FIG. 10. The oxygen electrode shown in these drawings has a rectangular shape, and a silicon substrate 101 has a dent 105 (105a, 105c, 105r) (corresponding to the sensitive portion of the oxygen electrode) formed by anisotropic etching. The depth of the dept portion 105C where the working electrode (cathode) is to be formed is different from the depth of the dent portions 105a or 105r where the counter electrode (anode) or the reference electrode is to be formed respectively. A working electrode 102, a reference electrode 103 and a counter electrode 104 are formed in each of the dent portion 105c, 105r and 105c respectively of the dent 105. The working electrode 102 is made of silver, the reference electrode 103 is made of silver/silver chloride, and the counter electrode 104 is made of gold. A gas-permeable film 107 is formed at the upper part of the dent 105 other than the portion of a through-hole 110. After this oxygen electrode is completed, 0.1M KCl aqueous solution as an electrolyte is filled into the dent 105 of the silicon substrate 101. A part of each of these electrodes 102, 103, 104 is extended outside from the dent 105 and forms a pad 106 on the surface of the substrate 101.

The oxygen electrode shown in these drawings can advantageously be produced in accordance with a production process which will be illustrated sequentially in FIG. 12. To have the present invention more easily understood, the following explanation will be given on the case where only one oxygen electrode is formed on one silicon wafer. It is to be noted, however, that a large number of oxygen electrodes are formed simultaneously in practice.

(1) Wafer washing:

A 3-in. diameter (100) plane silicon wafer 101 was prepared, and was washed with a mixed solution of hydrogen peroxide and ammonia, and then with concentrated nitric acid.

(2) Formation of $SiO_2$ film:

The silicon wafer was thermally oxidized while wet, and a 1.0 $\mu$m-thick $SiO_2$ film was formed on the entire surface of the silicon wafer 101.

(3) Formation of etching pattern:

A negative type photoresist ("OMR-83" (trade name), a product of Tokyo Oka K.K., viscosity=100 cps) was coated to a surface of the substrate, and then exposure, development and rinsing were carried out to form a resist pattern for etching on the wafer.

(4) Baking of substrate:

After the same negative type photoresist as the one used above was also coated to the back of the substrate, the substrate was baked at 150° C. in the course of 30 minutes.

(5) Etching of $SiO_2$ film:

The wafer was immersed in a 1:6 aqueous mixed solution of 50% hydrofluoric acid and 40% ammonium fluoride, and $SiO_2$ of exposed portions not covered with the photoresist was removed by etching. Subsequently, the resist was removed by a sulfuric acid/hydrogen peroxide (2:1) solution.

(6) Anisotropic etching of Si:

Anisotropic etching of silicon was carried out in a 35% aqueous potassium hydroxide solution at 80° C. In this case, etching was suspended at an intermediate stage in order to make the depth of the formation portion 105c of the working electrode 102 shallow or smaller than that of the formation portions 105a, 105r of the counter and reference electrodes 104, 103 as shown in FIG. 11. After the steps (1) to (5) were repeated once again, etching of the formation portions 105a, 105r of the counter and reference electrodes 104, 103 were carried out. The depth of the working electrode formation portion 105c was 20 $\mu$m and that of the counter and reference electrode formation portions 105a, 105r was 150 $\mu$m. Thereby, the mutual diffusion of a precursor, such as an intermediate material $OH^-$ formed on the cathode by the reaction: $O_2+2H_2O+4e \rightarrow 4OH^-$, or, a water soluble complex formed on the Ag anode by the reaction: $Ag+Cl^- \rightarrow AgCl+e$, $AgCl+nCl^- \rightarrow [AgCl_{n+1}]^{n-}$ complex, to the other electrode, particularly the diffusion or flow of the precursor formed on the anode to the reference electrode can be effectively limited or prevented by the shallow depth working electrode formation portion 105c of the dent 105. On the same reason, the distances of each of the electrodes are adjusted so that such mutual, diffusion or flow can be prevented.

Figure 12A:
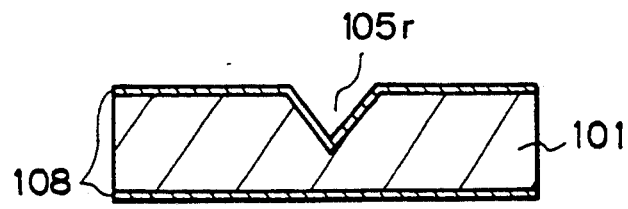

(7) Formation of $SiO_2$ layer:

After the substrate was washed, a 1 $\mu$m-thick $SiO_2$ layer (insulating layer) 108 was again formed by thermal oxidation. FIG. 12A shows the section of the substrate 101 (corresponding to the reference electrode formation portion 105r) after the treatment was carried out up to this stage.

(8) Formation of chromium and gold thin film:

A chromium thin film (400 Å, for the adhesion between gold and the substrate) and then a thin gold film (4,000 Å) were formed on the etched surface of the wafer 101 by vacuum deposition.

(9) Formation of resist pattern for counter electrode:

A resist pattern for forming the counter electrode 104 was formed on the thin gold film of the wafer by the use of a positive type photoresist ("OFPR-5000", trade name, a product of Tokyo Oka K.K., viscosity =50 cps).

(10) Etching of gold:

The substrate having the resist pattern thus formed thereon was immersed in a gold etching solution prepared by dissolving 4 g of KI and 1 g of $I_2$ in 40 ml of water, and the exposed gold portions were removed by etching. After the substrate was further washed with pure water, the resist was removed by acetone.

(11) Etching of chromium:

Next, the substrate was immersed in a chromium etching solution prepared by dissolving 0.5 g of NaOH and 1 g of $K_3Fe(CN)_6$ in 4 ml of water, and the exposed chromium layer was removed.

(12) Formation of silver thin film:

After the substrate having the gold pattern 104, 106a thus formed thereon was sufficiently washed, a thin silver film (4,000 Å) was formed by vacuum deposition. The counter electrode 104 was covered and protected during this vacuum deposition lest silver adhered to the counter electrode.

(13) Formation of working & reference electrode pattern:

A photoresist pattern for the working electrode 102 and the reference electrode 103 was formed in the same way as in (9).

(14) Etching of silver:

The substrate having the resist pattern formed thereon was immersed in an etching solution for silver which was a 1:1:20 solution of 29% aqueous ammonia, 31% hydrogen peroxide solution and pure water, and the exposed silver portions were removed by etching. Furthermore, after the substrate was washed with pure water, the resist was removed by acetone.

Figure 12B:
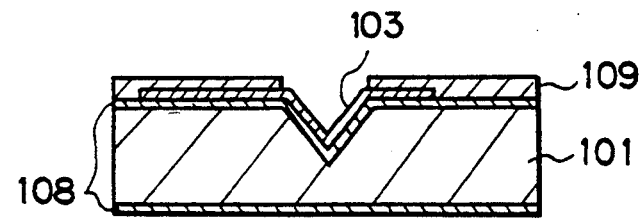

(15) Definition of electrode sensitive portion:

Portions other than the portion at which the oxygen electrode was to be formed (the electrode sensitive portion, that is, the portion anisotropically etched) and other than the pad portion 106, were covered with a negative type photoresist 109 ("OMR-83", viscosity =100 cps) (film thickness=2.8 $\mu$m). FIG. 12B shows the section of the substrate after the treatment described above so far was carried out.

Figure 12C:
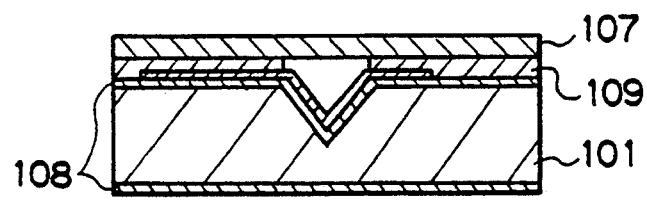

(16) Formation of gas-permeable film:

An FEP film 107 (a product of Toray Co., film thickness=12 $\mu$m) was applied by thermal fusing onto the sensitive portion except for the portion of the throughhole 110 as shown in FIG. 10. The temperature at this time was 280° C. FIG. 12C shows the section of the substrate for which the treatment described so far was carried out.

(17) Cut-out of substrates:

A large number of oxygen electrodes formed on the substrate were cut out into the chip form by the use of a dicing saw.

Figure 12D:
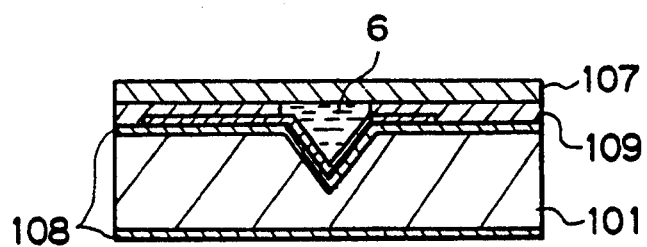

(18) Changing of electrolyte:

The main body of the oxygen electrode was dipped into 0.1M KCl aqoues solution placed into a beaker, and each beaker was exposed to a reduced pressure so that the electrolyte 6 was filled or charged into the sensitive portion from an open hole portion 110 (FIG. 12D). After this open hole portion 110 was closed by a vinyl tape, each oxygen electrode functioning was thus practically obtained.

The oxygen electrode completed in this manner operates by measuring a reduction current of oxygen generated from the working electrode 102 under the state where the sensitive portion is dipped into a buffer solution and a predetermined voltage is applied across the working electrode 102 and the reference electrode 103 (for example, with the application of $-0.6$ V to the working electrode with respect to the Ag/AgCl reference electrode). Apropos of this, the silver/silver chloride reference electrode can be formed by applying $-0.6$ V for 30 seconds to the working electrode 102, for example, before the start of use.

According to the present invention, the oxygen electrode which is simple both structurally and from the aspect of the production process can be obtained because the dent 105 for filling the electrolyte solution 6 and each electrode 102, 103, 104 constituting the oxygen electrode are formed on the same substrate. A mass-production of the oxygen electrodes becomes possible by employing a silicon wafer substrate, or the like.

Furthermore, since the oxygen electrode can be preserved under the dry state not containing the electrolyte, degradation of the electrode and the gas-permeable film which would otherwise be affected easily by the electrolyte does not occur so easily, and preservation for an extended period becomes possible.

Hereinafter, a biosensor and a biosensor assembly according to embodiments of the present invention will be explained with reference to the drawings.

First Embodiment (L-glutamic acid sensor)

Figure 13:
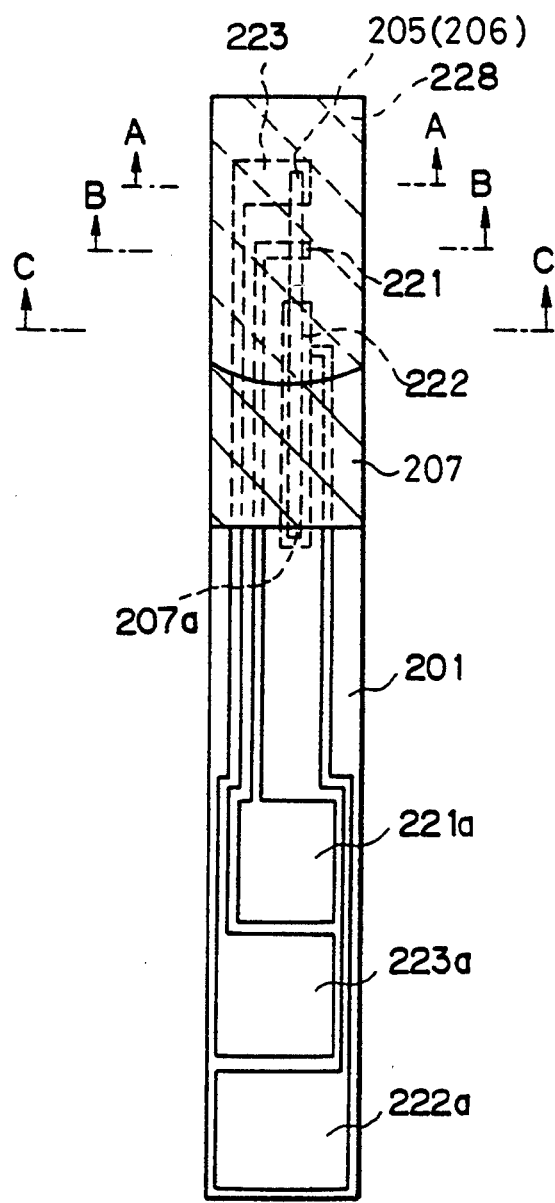
FIG. 13 is a plan view of a biosensor for L-glutamic acid according to an embodiment of the present invention.

Refer to FIGS. 13 and 14.

FIG. 13 is a plan view of a biosensor for L-glutamic acid according to an embodiment of the present invention. A rectangular dent 205 is formed on one of the surfaces of a substrate 201 consisting of a silicon sheet member having a shape of a rectangle of 15 mm×2 mm×0.4 mm, and the surface of both of the substrate 201 and the dent 205 is covered with an insulating film 201a. Two or three electrodes are formed on this insulating film 201a. In this embodiment, the electrodes 202 consist of a working electrode 221 made of silver, a counter electrode 222 made of gold and a reference electrode 223 made of silver/silver chloride. The principal portions of the dent 205 and the electrodes 202 are covered with a gas-permeable film 207 made of fluorinated ethylene propylene, and an electrolyte consisting of 0.1M KCl aqueous solution is filled into the dent 205. Reference numerals 221a, 222a and 223a denote connecting pads of the working electrode 221, counter electrode 222 and reference electrode 223, respectively. Reference numeral 207a denotes a through-hole for injecting the electrolyte 206, and reference numeral 208 denotes an enzyme- or microorganism-immobilizing film to which L-glutamic oxidase acid is immobilized.

Figure 14A:
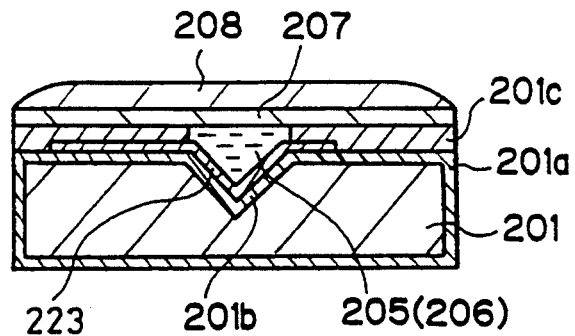
FIGS. 14A, 14B and 14C are a sectional view of the biosensor for L-glutamic acid shown in FIG. 13 taken along a line A—A, a sectional view taken along a line B—B and a sectional view taken along a line C—C of FIG. 13.
Figure 14B:
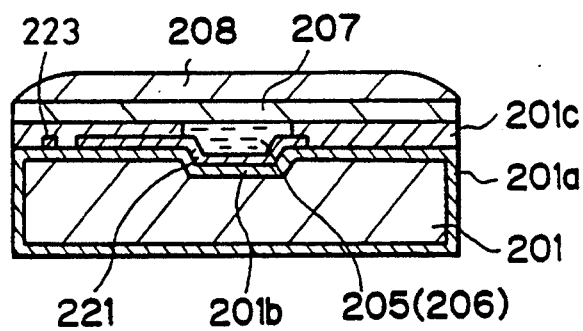
Figure 14C:
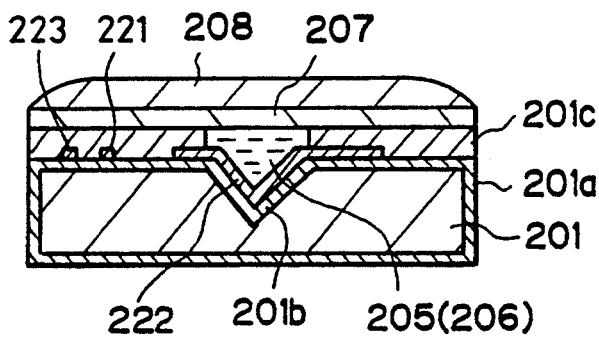

Refer to FIGS. 14A, 14B and 14C.

FIGS. 14A, 14B and 14C are a sectional view taken along a line A—A of the plan view shown in FIG. 14 (a sectional side view corresponding to the reference electrode 223), a sectional view taken along a line B—B (a sectional side view corresponding to the working electrode 221) and a sectional view taken along a line C—C (a sectional side view corresponding to the counter electrode 222), respectively. The reason why only the dent 205 corresponding to the working electrode 221 is shaped in a small depth is that if the reference electrode 223 is provided in addition to the working electrode 221 and the counter electrode 222, it becomes possible to prevent the product generated on the counter electrode 222 from flowing into the reference electrode 223 side (and vice versa), and this arrangement is desirable from the aspect of performance of the oxygen electrode.

Next, the production process will be explained.

Figure 15A:
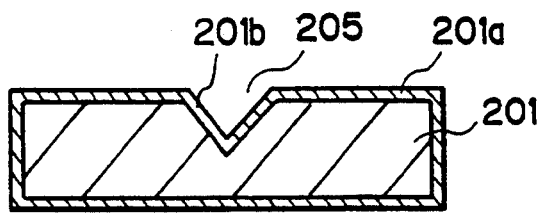
FIGS. 15A, 15B and 15C are sectional views showing step-wise the pre-stage (production process of an oxygen electrode) of the production process of the biosensor for glutamic acid according to the present invention.

Refer to FIG. 15A.

a) The silicon substrate 201 is washed with a mixed aqueous solution of hydrogen peroxide solution and aqueous ammonia and then with concentrated nitric acid.

b) The substrate is wet oxidized, and a 1.0 μm-thick silicon dioxide film 201a is formed on the entire surface of the substrate 201.

c) A negative type photoresist ("OMR-83", a trade name, a product of Tokyo Oka K.K.) is spin-coated. After exposure is carried out using a mask (not shown) having the shape of the dent 205, development is carried out so as to form a resist mask (not shown) for forming the dent.

d) The silicon dioxide film 201a is etched using this resist mask (not shown) and a mixed aqueous solution of hydrofluoric acid and ammonium fluoride as an etchant.

e) The silicon substrate 201 is etched anisotropically to form the dent 205 using the etched silicon dioxide film 201a as the mask and an aqueous potassium hydroxide solution as the etchant.

f) A 1 μm-thick silicon dioxide film 201b is deposited on the inner surface of the dent 205 thus etched anisotropically. This step can be carried out easily by oxidation.

Figure 15B:
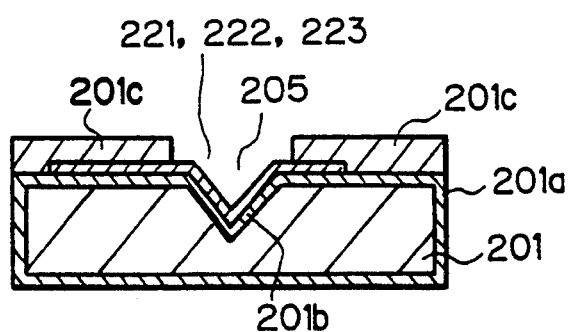
Figure 15C:
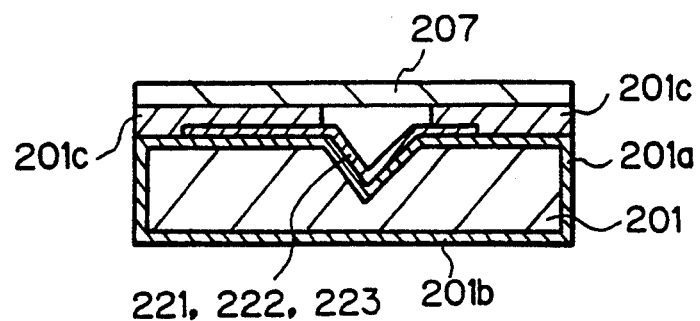
Figure 16A:
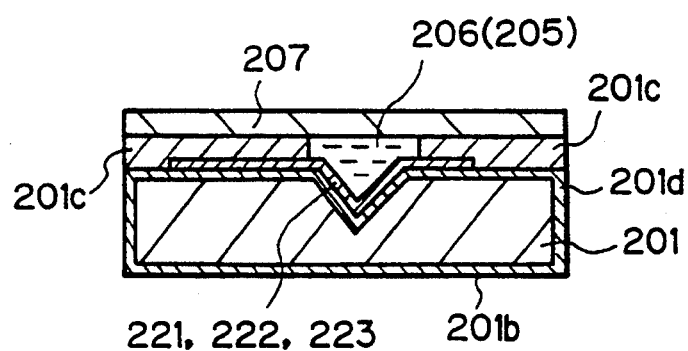
FIGS. 16A and 16B are sectional views showing step-wise the post-stage (production process of an enzyme or a microorganism immobilizing film) of the production process of the biosensor for glutamic acid according to an embodiment of the present invention.

Refer to FIG. 15B.

g) A 400 Å-thick chromium film (not shown) and a 4,000 Å-thick gold film (not shown) are formed.

h) A positive type resist ("OFPR-5000", trade name, a product of Tokyo Oka K.K.) is spin-coated, and a resist mask (not shown) for forming the counter electrode 222 is so formed as to remain only on a counter electrode formation region.

i) The counter electrode 222 is formed using a gold etching solution (an aqueous solution prepared by dissolving 4 g of potassium iodide and 1 g of iodine in 40 ml of water) and a chromium etching solution (an aqueous solution prepared by dissolving 0.5 g of sodium hydroxide and 1 g of potassium ferricyanide in 4 ml of water).

j) After the counter electrode 222 is covered with a photoresist, a 4,000 Å-thick silver film (not shown) is formed, and a resist mask (not shown) consisting of a positive type resist is formed on the working electrode formation region and on the reference electrode formation region.

k) The working electrode 221 and the reference electrode 223 are formed using a silver etching solution (a 1:1:20 aqueous solution of 29% aqueous ammonia, 31% hydrogen peroxide solution and pure water).

l) A negative type photoresist film 201c is formed on the portions other than the dent 205 and the pads 221a, 222a, 223a of the electrodes.
Refer to FIG. 15C.

m) The gas-permeable film 207 is formed by thermally fusing fluorinated ethylene propylene.
Refer to FIG. 16A.

n) The oxygen electrode produced in the manner described above is immersed in a 0.1M aqueous potassium chloride solution, and this aqueous potassium chloride solution is subjected to pressure reduction so as to substitute the air inside the dent 205 by the potassium chloride solution. The electrolyte is filled into the dent 205.

Figure 16B:
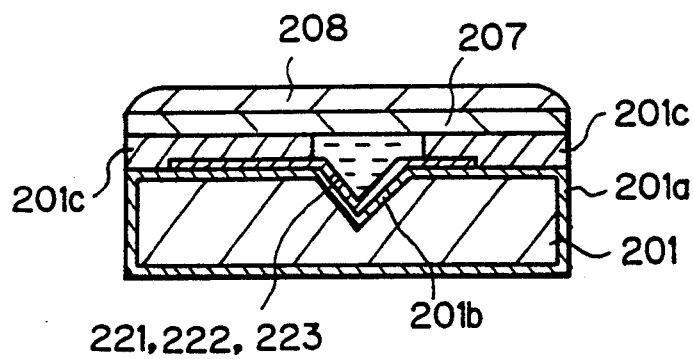
Figure 17:
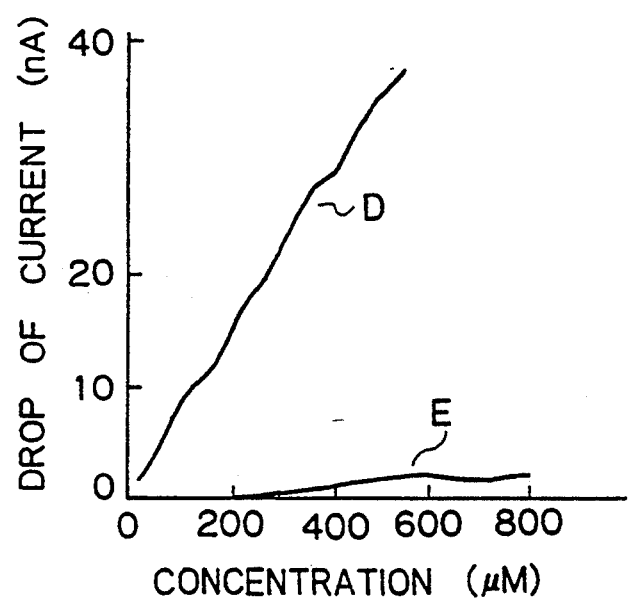
FIG. 17 shows the result of an effect confirmation test of the biosensor for glutamic acid (D) and the biosensor for lysine (E)
Figure 18:
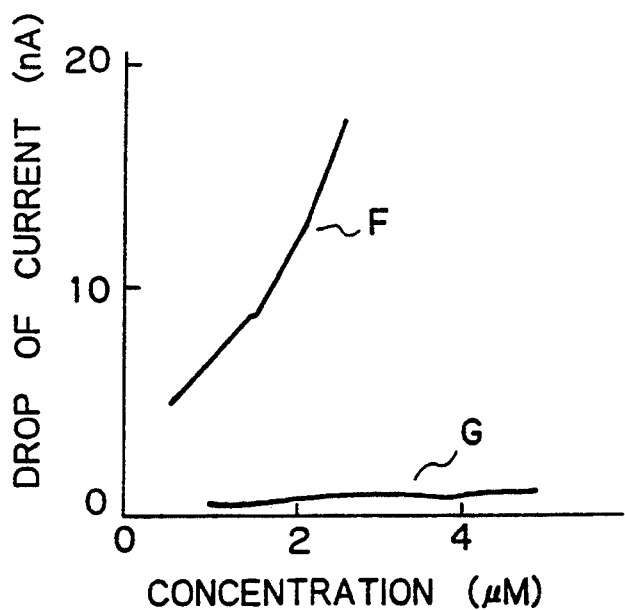
FIG. 18 shows the result of an effect confirmation test of the biosensor for hystidine (F) and the biosensor for alginine (G).

In order to suppress electro-chemical crosstalk between the electrodes and to obtain a better performance, it is recommended to let a gel be permeated with the electrolyte, and a gel of calcium alginate is suitable for this purpose. This gel layer can be formed inside the dent 205 by introducing the calcium chloride solution into the dent 205 by deairing, allowing calcium chloride to adhere to the dent 205 by baking, again effecting deairing so as to introduce the electrolyte of O,|M KCL aqueous solution containing sodium alginate into the dents 205. Due to this process, calcium chloride is eluted and geled in sodium alginate.
Refer to FIG. 16B.

o) 1 mg of L-glutamate oxidase, a product of Yamasa Shoyu K.K., is mixed with a mixed solution containing 5% of bovine serum albumin and 5% of glutaraldehyde, and this mixed solution is coated onto the gas-permeable film 207 so as to form an enzyme- or microorganism-immobilizing film 208.

Second Embodiment (L-lysine sensor)

An oxygen sensor explained with reference to FIG. 15C is produced in exactly the same way as in the first embodiment.

p) 0.1M aqueous calcium chloride solution is introduced into the dent 205 by deairing, and is then dried naturally so as to allow calcium chloride to adhere into the dent 205.

q) Deairing is carried out once again so as to introduce an aqueous sodium alginate solution containing 0.1M potassium chloride and an independent nutrient bacteria ($1.5 \times 10^8$ ml$^{-1}$) assimilating carbon dioxide gas.

r) Air bubbles entrapped into the dents 205 simultaneously with the electrolyte are removed by centrifugal separation.

s) A mixed solution of 2 mg of L-lysine decarboxylase (a product of SIGMA Co.) with a mixed solution containing 5% of bovine serum albumin and 5% of glutaraldehyde is coated and immobilized onto the gas-permeable film 207.

The L-lysine sensor produced in this manner operates in the manner described below and detects the concentration of L-lysine. To begin with, while the sensor is immersed in a buffer solution, L-lysine is added. Then, L-lysine is decomposed by the enzyme and dissociates the carbon dioxide gas. The independent nutrient bacteria assimilating the carbon dioxide gas assimilates the carbon dioxide gas and simultaneously consumes oxygen. After all, since the amount of oxygen changes, the concentration of L-lysine can be detected.

Third Embodiment (Biosensor assembly of detecting concentrations of two kinds of amino acids)

Oxygen electrodes similar to those described above are bonded back to back. The independent nutrient bacteria is immobilized into the dent 205, and two kinds of enzymes selected from the group consisting of L-alginin decarboxylase, L-lysine decarboxylase and L-histidine decarboxylase, for example, are introduced to the gas-permeable film 207. In this manner, the concentrations of two kinds of amino acids can be detected by a single biosensor.

Fourth Embodiment (Biosensor assembly for detecting concentration of many kinds of amino acids)

A plurality of oxygen electrodes similar to those described above are integrated on a single substrate, and the independent nutrient bacteria is immobilized into the dent 205 of each of the oxygen electrodes. L-alginin decarboxylase, L-lysine decarboxylase and L-histidine decarboxylase, for example, are immobilized onto the gas-permeable film 207, or instead of immobilizing the microorganisms, L-glutamate oxidase is immobilized onto the gas-permeable film 207. In this manner, the concentration of a plurality of kinds of amino acids can be detected by a single biosensor.

Fifth and Sixth Embodiments

The fifth embodiment relates to an embodiment wherein an enzyme- or microorganism-immobilizing film having enzymes or microorganisms immobilized thereto is formed between the dent 205 of the substrate 201 and the gas-permeable film 207.

The sixth embodiment relates to another embodiment wherein an enzyme- or microorganism-immobilizing film having enzymes or microorganisms immobilized thereto is formed between the dent of the substrate and the gas-permeable film. Furthermore, an enzyme- or microorganism-immobilizing film having enzymes or microorganisms immobilized thereto is formed on the gas-permeable film 207.

These embodiments are effective when the object of measurement is a volatile matter or a gaseous matter.

As described above, the biosensor according to the present invention skillfully combines the photolithographic technique and the anisotropic etching technique widely employed in the semiconductor fabrication technology. Accordingly, the biosensor according to the present invention is extremely small in size, can be handled easily, and moreover, has excellent performance. The gas-permeable film 207 is formed by thermally fusing fluorinated ethylene propylene and is very tough. Furthermore, since the bubbles entrapped in the electrolyte solution are removed by centrifugal separation, the production yield is high.

We claim:

1. An oxygen electrode comprising:

a flat electrode substrate having at least a working electrode and a counter electrode formed thereon a container substrate having dents formed to confront said working electrode and said counter electrode and having fine grooves for connecting said dents to one another said dents and said fine grooves containing an electrolyte containing water therein, said container substrate being bonded to said flat electrode substrate, wherein of said dents, said dent confronting said working electrode has a through hole extending to a side opposite to said flat electrode substrate; and a gas-permeable film which is impermeable to said electrolyte containing water, is formed to cover said through hole.

2. An oxygen electrode as set forth in claim 1, further comprising:
a reference electrode formed on said flat electrode substrate, and
an electrolyte-injecting dent formed on said container substrate to confront said reference electrode.

3. An oxygen electrode as set forth in claim 2, wherein said working electrode and said counter electrode formed on said flat electrode substrate are separated from one another by such a distance that said working and counter electrodes are not influenced by products formed on their respective surfaces.

4. An oxygen electrode as set forth in claim 2, further comprising an additional elongated groove for connecting said electrolyte injecting dent to said other dents.

5. An oxygen electrode as set forth in claim 2, wherein each of said dents is formed on the peripheral edge portion of the through hole on the surface, opposite to the bonded surface, of said container substrate, and each of said dents is covered with said gas-permeable film.

6. An oxygen electrode as set forth in claim 2, wherein said flat electrode substrate is selected from the group consisting of a borosilicate glass substrate, a lead glass substrate, a silicon substrate having, formed on the surface thereof, a film of a borosilicate glass, a silicon substrate having, formed on the surface thereof, a film of a lead glass, a glass substrate having, formed on the surface thereof, a film of a borosilicate glass containing a Pyrex glass, a glass substrate having, formed on the surface thereof, a film of a lead glass, and a silicon substrate having, formed on the surface thereof, a thermal oxidation film.

7. An oxygen electrode as set forth in claim 2, wherein said working and counter electrodes are formed in a shallow groove formed on said flat electrode substrate by etching in accordance with an electrode pattern of said working and counter electrodes.

8. An oxygen electrode as set forth in claim 2, wherein said container substrate is a (100) plane silicon substrate.

9. An oxygen electrode as set forth in claim 2, further comprising a pad formed at one end of each of said working and counter electrodes, wherein said pad has a size such that a socket terminal of an integrated circuit (IC) is directly gripped in said pad.

10. An oxygen electrode as set forth in claim 1, wherein said working electrode and said counter electrode formed on said flat electrode substrate are separated from one another by such a distance that said working and counter electrodes are not influenced by products formed on their respective surfaces.

11. An oxygen electrode as set forth in claim 1, wherein each of said dents is formed on the peripheral edge portion of the through hole on the surface, opposite to the bonded surface, of said container substrate, and each of said dents is covered with said gas-permeable film.

12. An oxygen electrode as set forth in claim 1, wherein said flat electrode substrate is selected from the group consisting of a borosilicate glass substrate, a lead glass substrate, a silicon substrate having, formed on the surface thereof, a film of a borosilicate glass, a silicon substrate having, formed on the surface thereof, a film of a lead glass, a glass substrate having, formed on the surface thereof, a film of a borosilicate glass containing a Pyrex glass, a glass substrate having, formed on the surface thereof, a film of a lead glass, and a silicon substrate having, formed on the surface thereof, a thermal oxidation film.

13. An oxygen electrode as set forth in claim 1, wherein said working and counter electrodes are formed in a shallow groove formed on said flat electrode substrate by etching in accordance with an electrode pattern of said working and counter electrodes.

14. An oxygen electrode as set forth in claim 1, wherein said container substrate is a (100) plane silicon substrate.

15. An oxygen electrode as set forth in claim 1, wherein said gas-permeable film is a fluorinated ethylene propylene (FEP) film.

16. An oxygen electrode as set forth in claim 1, further comprising a pad formed at one end of each of said working and counter electrodes, wherein said pad has a size such that a socket terminal of an integrated circuit (IC) is directly gripped in said pad.

17. An oxygen electrode comprising:
an electrode substrate having first and second electrodes formed thereon;
a container substrate having dents which confront said first and second electrodes and an elongated grove for connecting the dents to one another, said dents and said elongated groove containing an electrolyte containing water therein, said container substrate being bonded to said electrode substrate so that said dent confronting said first electrode has a through hole extending to a side opposite said electrode substrate; and
a gas-permeable film which is impermeable to said electrolyte containing water, covering said through hole.

18. An oxygen electrode comprising:
a dent covered with an insulating film formed on one of the surfaces of a substrate;
a plurality of electrodes formed in a mutually spaced-apart relation at a bottom portion of said dent;
an electrolyte filled in said dent; and
a gas-permeable film formed at portions where said electrodes are formed, other than a through-hole for injecting said electrolyte, in such a manner as to cover said dent.

19. An oxygen electrode according to claim 18, wherein said substrate on which said dent is to be formed is a silicon substrate or a glass substrate.

20. An oxygen electrode according to claim 18, which includes a reference electrode in addition to a working electrode and a counter electrode.

21. An oxygen electrode according to claim 18, wherein said gas-permeable film is a film of fluorinated ethylene propylene resin.

22. A biosensor comprising:
a dent covered with an insulating film formed on one of the surfaces of a substrate;
a plurality of electrodes formed in a mutually spaced-part relation at a bottom portion of said dent;
an electrolyte filled in said dent;
a gas-permeable film formed at portions where said electrodes are formed, other than at a through-hole for injecting said electrolyte, in such a manner as to cover said dent; and
at least one layer of an enzyme- or microorganism-immobilizing film formed on said gas-permeable film.

23. A biosensor comprising:
a dent covered with an insulating film formed on one of the surfaces of a substrate;

a plurality of electrodes formed in a mutually spaced-part relation at a bottom portion of said dent;

an electrolyte filled in said dent;

a gas-permeable film formed at portions where said electrodes are formed, other than a through-hole for injecting said electrolyte, in such a manner as to cover said dent; and an enzyme or a microorganism-immobilizing film formed between said dent and said gas-permeable film.

24. A biosensor comprising:

a dent covered with an insulating film formed on one of the surfaces of a substrate;

a plurality of electrodes formed in a mutually spaced-part relation at a bottom portion of said dent;

an electrolyte filled in said dent;

a gas-permeable film formed at portions where said electrodes are formed, other than at a through-hole for injecting said electrolyte, in such a manner as to cover said dent;

a first enzyme- or microorganism-immobilizing film formed between said dent and said gas-permeable film; and a second enzyme- or microorganism-immobilizing film formed on said gas-permeable film.

* * * * *